United States Patent [19]

Baltruschat et al.

[11] 4,319,918
[45] Mar. 16, 1982

[54] α-SUBSTITUTED N-(TRIMETHYLCYCLOALKENYL)-N-ALKYLACETAMIDES AND THEIR USE IN PHYTOTOXIC PREPARATIONS

[75] Inventors: Helmut Baltruschat; Hans Bellut, both of Dülmen; Horst Schnurbusch, Herne, all of Fed. Rep. of Germany

[73] Assignees: Chemische Werke Huls Aktiengesellschaft, Marl; Ruhr-Stickstoff Aktiengesellschaft, Bochum, both of Fed. Rep. of Germany

[21] Appl. No.: 108,226

[22] Filed: Dec. 28, 1979

[30] Foreign Application Priority Data

Dec. 29, 1978 [DE] Fed. Rep. of Germany ....... 2856651
Oct. 4, 1979 [DE] Fed. Rep. of Germany ....... 2940231

[51] Int. Cl.³ .................... A01N 37/18; C07C 103/37; C07C 103/727
[52] U.S. Cl. ..................................... 71/118; 564/210; 564/217
[58] Field of Search ................... 71/118; 564/210, 217

[56] References Cited

U.S. PATENT DOCUMENTS 3,586,496  6/1971  Chupp ................................ 71/118

*Primary Examiner*—Catherine L. Mills
*Attorney, Agent, or Firm*—Oblon, Fisher, Spivak, McClelland & Maier

[57] ABSTRACT

Herbicidal-substituted α-(trimethylcycloalkenyl)-N-alkylacetamides of the formula

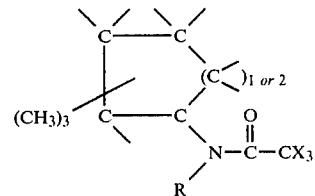

wherein R is a linear or branched alkyl or alkoxyalkyl radical with 1–6 carbon atoms or an allyl radical, optionally substituted with $C_1$–$C_4$ alkylene groups, and X is a substituent from the group consisting of hydrogen, methyl, chlorine and bromine, in any combination, the free valences signify hydrogen and two of the methyl groups on the ring are attached to the same carbon atom, are useful pre- and post-emergent herbicides for weed control in crops.

18 Claims, No Drawings

α-SUBSTITUTED N-(TRIMETHYLCYCLOALKENYL)-N-ALKYLACETAMIDES AND THEIR USE IN PHYTOTOXIC PREPARATIONS

BACKGROUND OF THE INVENTION

1. Field of the Invention

This invention relates to herbicides and more particularly to substituted N-(trimethylcycloalkenyl)-N-alkylacetamides. The invention also relates to phytotoxic compositions containing such herbicides and to methods using the herbicides in the prevention of weeds by treating crops.

2. Description of the Prior Art

A great variety of organic and inorganic compounds have been found to be useful as herbicides. Certain N-substituted acetamides have been found to have herbicidal properties, and some have been used commercially. Such herbicidal substituted acetamides are disclosed, for example, in U.S. Pat. No. 2,864,683, U.S. Pat. No. 3,707,366, German Offenlegungsschrift No. 25 26 868, and German Offenlegungsschrift No. 20 45 380. Certain N-alkenylacetamides and N-cycloalkenylacetamides are also known compounds, and their usefulness as both pre-emergent and post-emergent herbicides has been described. However, because of the great variety of useful plants and of weeds, and because of certain deficiencies of the known herbicides, research is continuing for the purpose of discovering more useful herbicidal compounds. Effectiveness against a wide variety of weeds (broad-spectrum activity), high potency, and ability to kill weeds without harming useful crops (selectivity) are properties which are desirable in an herbicide. However, known herbicides do not possess these properties to the extent which is desirable. Hence a need has continued to exist for herbicidal compounds having an improved combination of broad-spectrum activity, high potency, and selectivity.

SUMMARY OF THE INVENTION

Accordingly, it is an object of the invention to provide improved herbicidal compounds.

A further object is to provide herbicidal compounds which have a desirable combination of broad-spectrum activity, high potency, and selectivity.

A further object is to provide novel N-(trimethylcycloalkenyl)-N-alkylacetamides which have good herbicidal properties.

Further objects of the invention will become apparent from the description of the invention which follows.

A further object is to provide herbicidal compositions containing novel N-(trimethylcycloalkenyl)-N-alkylacetamides.

A further object is to provide a method of selectively killing weeds growing among crops by treating with novel N-(trimethylcycloalkenyl)-N-alkylacetamides.

The novel herbicidal compounds of this invention are α-substituted N-(trimethylcycloalkenyl)-N-alkylacetamides of the formula:

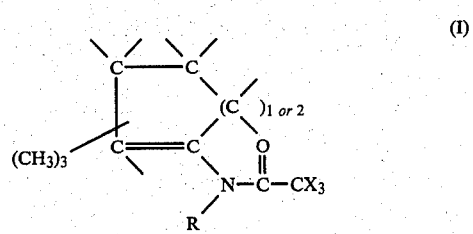

wherein R is a linear or branched alkyl or alkoxyalkyl radical with 1–6 carbon atoms or an allyl radical, optionally substituted with $C_1$–$C_4$ alkyl groups, X is a substituent selected from the group consisting of hydrogen, methyl, chlorine, and bromine, in any combination, the free valences signify hydrogen, and two of the methyl groups on the ring are attached to the same carbon atom.

The novel α-substituted N-(trimethylcycloalkenyl)-N-alkylacetamides of this invention can be combined with conventional adjuvants such as diluents, carriers, fillers, wetting agents, dispersants and emulsifiers to form herbicidal compositions which can be applied to crops to selectively kill weeds.

DETAILED DESCRIPTION OF THE PREFERRED EMBODIMENTS

The new α-substituted N-(trimethylcycloalkenyl)-N-alkylacetamides can be synthesized using known procedures. According to a suitable method, a cyclic ketone of the formula (II) is first reacted with an amine of the formula (III) with elimination of water to form the corresponding azomethine of formula (IV).

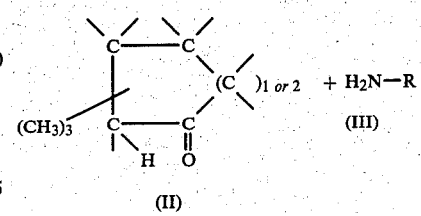

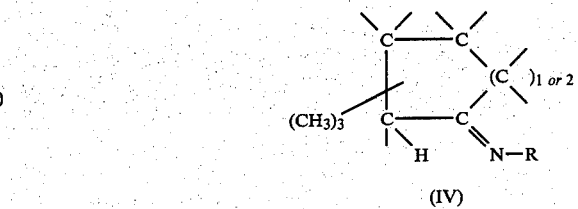

These azomethines are then reacted in a further step with α-substituted acetyl halides of the formula V in the presence of an acid-neutralizing agent.

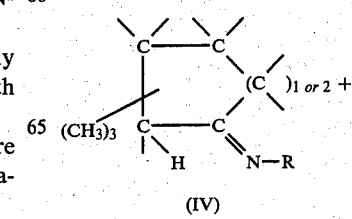

-continued

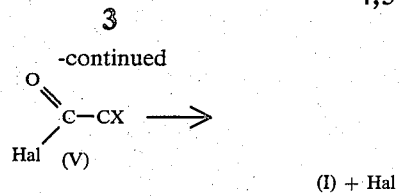

(I) + Hal

In formula (V) Hal represents the halogens chlorine and bromine, preferably, however, chlorine.

As starting materials of the formula II in the preparation of the azomethines of formula IV, cyclopentanones and cyclohexanones which have a hydrogen atom on at least one of the two α-carbon atoms can be used. Furthermore, it is important for the new acetamides that two of the methyl groups in the ring of the cyclic ketone be attached to the same carbon atom, that is, be geminal. Ketones which are readily commercially available, such as 3,5,5-trimethylcyclohexanone, 2,2,4-cyclopentanone, 2,4,4-cyclopentanone, etc. are preferred. Since in the preparation of these particular cyclic ketones mixtures of isomers are generally obtained, they are also preferably used as their technical-grade mixtures.

Suitable compounds for reacting with the above-described cyclic ketones are the primary amines having linear or branched alkyl and alkoxyalkyl radicals with 1-6 carbon atoms, such as methylamine, ethylamine, n- and i-propylamine, n-, i-, and tert-butylamine, pentylamines, hexylamines, and allylamines. Methoxy- and ethoxyethylamines are also suitable. Radicals having 1-4 carbon atoms are preferred. The reaction of the ketones of formula II with the primary amines to produce the azomethines of formula IV can be carried out by known procedures, as by removing the product water by azeotropic distillation. Inert solvents are suitable, that is, those which react neither with the starting materials nor with the final products, for example, aromatics, such as benzene, toluene, xylenes, chlorbenzene, tetrahydronaphthalene and the like, dialkyl ethers, and chlorinated aliphatics. It is also possible to use the starting ketone of the reaction in excess as a carrier. The reaction temperature will depend upon the carrier agent used for eliminating the water.

The elimination of the water can be catalytically accelerated by addition of acid or acid reactive catalysts, such as hydrochloric and hydrocyanic acids, ammonium sulfate, and zinc chloride, or basic compounds such as KOH, NaOH, and alkali carbonates. Frequently, with sterically hindered reagents, it is advantageous to remove the water produced by the reaction continuously using molecular seives.

The azomethines of formula IV, usually without special purification, are then immediately reacted with the substituted acetyl halides of formula V in the presence of acid neutralizing agents, such as tertiary amines, pyridine bases, or alkali metal carbonates. In a variation of the method, the hydrochloric acid produced is driven off by boiling. Chloroacetyl chloride is the preferred acetyl halide.

The addition of the acetyl group to the azomethine double bond is carried out conveniently in a temperature range of 0°-160° C., preferably at 0°-20° C.

Isolation of the N-(trimethylcycloalkenyl)-N-alkylacetamides of the invention is carried out, after optional removal of the precipitated halide by filtration, by distillative workup of the mixture to remove the solvent used in the previous reaction step. The purification of the acetamides so obtained can then be carried out by recrystallization from other suitable solvents, such as formamide or alcohols.

When unsymmetrical ketones are used, the resulting double bond in the cycloalkyl ring can be formed in two different positions, provided that both α-carbon atoms in the ring have at least one hydrogen atom. The reaction product then contains a mixture of isomeric compounds of formula I which differ only in the location of the double bond. However, this has no effect on the biological activity.

Depending on the arrangement of the methyl groups on the ring and the substitution on the acetamide group, the compounds of formula I are liquid or crystalline materials.

The preparation of the new N-(trimethylcycloalkenyl)-N-alkylacetamides will be illustrated by the following examples.

EXAMPLE 1

Eight hundred forty parts by weight (6 moles) of 3,3,5-trimethylcyclohexanone were dissolved in 6 liters of benzene and 2 parts by weight of ammonium sulfate were added. Into this solution 186 parts (6 moles) of gaseous methylamine were led at 0° C. After standing for 18 hours a second, aqueous, phase formed and was separated. The remaining water was removed by boiling in a water separator. The benzene solution of azomethine so obtained was then slowly treated with 678 parts by weight (6 moles) of chloroacetylchloride at room temperature with stirring, and after one hour 667 parts by weight (6.6 moles) of triethylamine were added. After a further hour of stirring the precipitated hydrochloride salt was filtered off, and the filtrate was washed with water until free of chloride and distilled under vacuum.

After removal of the solvent an oily yellow liquid was obtained (B.P.=130°-145° C. at 1.5 torr) which darkened with the passage of time ($n_D^{20}$=1.4942). When this was allowed to stand, crystals having a M.P. of 34° C. slowly separated. The yield through all steps amounted to 766 parts by weight of a mixture of N-(3,3,5-trimethylcyclohexen-1-yl)-N-methyl-α-chloroacetamide and N-(3,5,5-trimethylcyclohexen-1-yl)-N-methyl-α-chloroacetamide having a molecular weight of 213 (229) and 15.1% (15.3%) of organically combined chlorine. (The corresponding calculated values are given in parentheses.)

EXAMPLE 2

By the same procedure as in Example 1 using a mixture comprising 2,2,4-trimethylcyclopentanone and 2,4,4-trimethylcyclopentanone (about 1:1) (25.2 parts by weight) in 150 milliliters of benzene, one part by weight of ammonium sulfate and 6.2 parts by weight of methylamine, further reacted with 22.6 parts by weight of chloroacetyl chloride and 24.6 parts by weight of trimethylamine, a mixture of isomers consisting of N-(3,3,5-trimethylcyclopenten-1-yl)-N-methyl-α-chloroacetamide, N-(3,5,5-trimethylcyclopenten-1-yl)-N-methyl-α-chloroacetamide, and N-(2,4,4-trimethylcyclopenten-1-yl)-N-methyl-α-chloroacetamide was obtained. The yield of partially crystalline dark brown product amounted to 33 parts by weight. The molecular weight was determined to be 198 (215). The content of organically combined chlorine was 17.5% (16.5%). The nitrogen content was 6.3% (6.5%).

EXAMPLES 3-62

Following the procedure of Example 1 additional N-(trimethylcycloalkenyl)-N-alkylacetamides were prepared. The starting materials for the syntheses can be selected from the following summary.

| Example No. | Ketone (1 mole) | Amine (1 mole) | Substituted Acetyl chloride (1 mole) |
|---|---|---|---|
| 3 | 3,3,5-Trimethylcyclohexanone | $CH_3NH_2$ | $Cl_2CH-COCl$ |
| 4 | 3,3,5-Trimethylcyclohexanone | " | $Cl_3C-COCl$ |
| 5 | 3,3,5-Trimethylcyclohexanone | " | $(CH_3)_3C-COCl$ |
| 6 | 3,3,5-Trimethylcyclohexanone | " | $CH_3CCl_2-COCl$ |
| 7 | 3,3,5-Trimethylcyclohexanone | " | $CH_3-COCl$ |
| 8 | 3,3,5-Trimethylcyclohexanone | $C_2H_5NH_2$ | $ClCH_2-COCl$ |
| 9 | 3,3,5-Trimethylcyclohexanone | " | $Cl_2CH-COCl$ |
| 10 | 3,3,5-Trimethylcyclohexanone | " | $Cl_3C-COCl$ |
| 11 | 3,3,5-Trimethylcyclohexanone | " | $(CH_3)_3C-COCl$ |
| 12 | 3,3,5-Trimethylcyclohexanone | " | $CH_3CCl_2-COCl$ |
| 13 | 3,3,5-Trimethylcyclohexanone | " | $CH_3-COCl$ |
| 14 | 3,3,5-Trimethylcyclohexanone | $(CH_3)_2CHNH_2$ | $ClCH_2-COCl$ |
| 15 | 3,3,5-Trimethylcyclohexanone | " | $Cl_2CH-COCl$ |
| 16 | 3,3,5-Trimethylcyclohexanone | " | $Cl_3C-COCl$ |
| 17 | 3,3,5-Trimethylcyclohexanone | " | $(CH_3)_3C-COCl$ |
| 18 | 3,3,5-Trimethylcyclohexanone | " | $CH_3CCl_2-COCl$ |
| 19 | 3,3,5-Trimethylcyclohexanone | " | $CH_3-COCl$ |
| 20 | 3,3,5-Trimethylcyclohexaone | $i-C_4H_9NH_2$ | $ClCH_2-COCl$ |
| 21 | 3,3,5-Trimethylcyclohexanone | " | $Cl_2CH-COCl$ |
| 22 | 3,3,5-Trimethylcyclohexanone | " | $Cl_3C-COCl$ |
| 23 | 3,3,5-Trimethylcyclohexanone | " | $(CH_3)_3C-COCl$ |
| 24 | 3,3,5-Trimethylcyclohexanone | " | $CH_3CCl_2-COCl$ |
| 25 | 3,3,5-Trimethylcyclohexaone | " | $CH_3-COCl$ |
| 26 | 2,2,4- und 2,4,4-Trimethylcyclopentanone(1:1) | $CH_3NH_2$ | $Cl_2CH-COCl$ |
| 27 | 2,2,4- und 2,4,4-Trimethylcyclopentanone(1:1) | " | $Cl_3C-COCl$ |
| 28 | 2,2,4- und 2,4,4-Trimethylcyclopentanone(1:1) | " | $(CH_3)_3C-COCl$ |
| 29 | 2,2,4- und 2,4,4-Trimethylcyclopentanone(1:1) | " | $CH_3CCl_2-COCl$ |
| 30 | 2,2,4- und 2,4,4-Trimethylcyclopentanone(1:1) | " | $CH_3-COCl$ |
| 31 | 2,2,4- und 2,4,4-Trimethylcyclopentanone(1:1) | $C_2H_5NH_2$ | $ClCH_2-COCl$ |
| 32 | 2,2,4- und 2,4,4-Trimethylcyclopentanone(1:1) | " | $Cl_2CH-COCl$ |
| 33 | 2,2,4- und 2,4,4-Trimethylcyclopentanone(1:1) | " | $Cl_3C-COCl$ |
| 34 | 2,2,4- und 2,4,4-Trimethylcyclopentanone(1:1) | " | $(CH_3)_3-COCl$ |
| 35 | 2,2,4- und 2,4,4-Trimethylcyclopentanone(1:1) | " | $CH_3CCl_2-COCl$ |
| 36 | 2,2,4- und 2,4,4-Trimethylcyclopentanone(1:1) | " | $CH_3-COCl$ |
| 37 | 2,2,4- und 2,4,4-Trimethylcyclopentanone(1:1) | $(CH_3)_2CHNH_2$ | $ClCH_2-COCl$ |
| 38 | 2,2,4- und 2,4,4-Trimethylcyclopentanone(1:1) | " | $Cl_2CH-COCl$ |
| 39 | 2,2,4- und 2,4,4-Trimethylcyclopentanone(1:1) | " | $Cl_3C-COCl$ |
| 40 | 2,2,4- und 2,4,4-Trimethylcyclopentanone(1:1) | " | $(CH_3)_3C-COCl$ |
| 41 | 2,2,4- und 2,4,4-Trimethylcyclopentanone(1:1) | " | $CH_3CCl_2-COCl$ |
| 42 | 2,2,4- und 2,4,4-Trimethylcyclopentanone(1:1) | " | $CH_3-COCl$ |
| 43 | 2,2,4- und 2,4,4-Trimethylcyclopentanone(1:1) | $i-C_4H_9NH_2$ | $ClCH_2-COCl$ |
| 44 | 2,2,4- und 2,4,4-Trimethylcyclopentanone(1:1) | " | $Cl_2CH-COCl$ |
| 45 | 2,2,4- und 2,4,4-Trimethylcyclopentanone(1:1) | " | $Cl_3C-COCl$ |
| 46 | 2,2,4- und 2,4,4-Trimethylcyclopentanone(1:1) | " | $(CH_3)_3C-COCl$ |
| 47 | 2,2,4- und 2,4,4-Trimethylcyclopentanone(1:1) | " | $CH_3CCl_2-COCl$ |
| 48 | 2,2,4- und 2,4,4-Trimethylcyclopentanone(1:1) | " | $CH_3-COCl$ |
| 49 | 3,3,5-Trimethylcyclohexanone | $n-C_4H_9NH_2$ | $ClCH_2-COCl$ |
| 50 | 2,2,4- und 2,4,4-Trimethylcyclopentanone(1:1) | " | " |
| 51 | 3,3,5-Trimethylcyclohexanone | $CH_3OC_2H_4NH_2$ | " |
| 52 | 3,3,5-Trimethylcyclohex-2-enone | " | " |
| 53 | 3,3,5-Trimethylcyclohex-2-enone | $C_2H_5OC_2H_4NH_2$ | " |
| 54 | 3,3,5-Trimethylcyclohexaone | " | " |
| 55 | 3,3,5-Trimethylcyclohexanone | $CH_3OC_3H_6NH_2$ | " |
| 56 | 3,3,5-Trimethylcyclohexanone | $C_2H_5OC_3H_6NH_2$ | " |
| 57 | 3,3,5-Trimethylcyclohexanone | $C_4H_9OC_3H_6NH_2$ | " |
| 58 | 3,3,5-Trimethylcyclohexanone | $CH_3NH_2$ | $Br CH_2-COCl$ |
| 59 | 3,3,5-Trimethylcyclohexanone | $C_2H_5NH_2$ | " |
| 60 | 3,3,5-Trimethylcyclohexanone | $(CH_3)_2CHCH_2NH_2$ | " |
| 61 | 2,2,4- und 2,4,4-Trimethylcyclopentanone(1:1) | $CH_3NH_2$ | " |
| 62 | 3,3,5-Trimethylcyclohexanone | $CH_3OC_2H_4NH_2$ | " |

EXAMPLE 63

To 28 parts by weight (0.2 mole) of 3,3,5-trimethylcyclohexanone, dissolved in 0.25 liter of benzene, to which 0.1 part by weight of ammonium sulfate had been added, 11.4 parts by weight (0.2 moles) of allylamine were added. The water was removed by boiling in a water separator. The benzene solution of azomethine so obtained was then gradually reacted with 22.6 parts by weight (0.2 moles) of chloroacetyl chloride, dissolved in 0.05 liter of benzene, at room temperature with stirring, and after one hour 22 parts by weight (0.2 moles) of triethylamine, dissolved in 0.1 liter of benzene, was added. After a further hour of stirring the precipitated hydrochloride salt was filtered off, and the filtrate was washed with water until free of chlorine and distilled under vacuum.

After removal of the solvent, an orange oily liquid (B.P. = 103°–108° C. at 1.0 torr) was obtained which darkened with the passage of time ($n_D^{20} = 1.4974$). The yield through all steps amounted to 36 parts by weight of a mixture of N-(3,3,5-trimethylcyclohexen-1-yl)-N-allyl-α-chloroacetamide and N-(3,5,5-trimethylcyclohexen-1-yl)-N-allyl-α-chloroacetamide having a molecular weight of 230 (255) and 14.8% (13.9%) or organically combined chlorine. The corresponding calculated values are given in parentheses.

EXAMPLE 64

By the same procedure as in Example 63 using a mixture comprising 2,2,4-trimethylcyclopentanone and 2,4,4-trimethylcyclopentanone (about 1:1) (25.2 parts by weight; 0.2 mole) in 0.2 liter of benzene, 0.1 part by weight of ammonium sulfate, and 11.4 parts by weight (0.2 mole) of allylamine, further reacted with 22.6 parts by weight (0.2 mole) of chloracetyl chloride in 0.05 liter of benzene and 22 parts by weight (0.2 mole) of triethylamine in 0.1 liter of benzene, a mixture of isomers consisting of N-(3,3,5-trimethylcyclopenten-1-yl)-N-allyl-α-chloroacetamide, N-(3,5,5-trimethylcyclopenten-1-yl)-N-allyl-α-chloroacetamide, and N-(2,4,4-trimethylcyclopenten-1-yl)-N-allyl-α-chloroacetamide was obtained. The yield of brown oily distillate (B.P. = 88°–93° C. at 1.0 torr) having a refractive index ($n_D^{20} = 1.4978$) was 29 parts by weight. The content of organically combined chlorine was 15.9% (14.7%). The nitrogen content was 6.1% (5.8%).

EXAMPLES 63, 64, 65 AND 66

By the same procedures as in Example 63 additional N-(trimethylcycloalkenyl)-N-alkylacetamides were prepared. The starting materials for the syntheses can be selected from the following summary.

| Example No. | Ketone (1 mole) | Amine (1 mole) | Substituted Acetyl chloride (1 mole) |
|---|---|---|---|
| 63 | 3,3,5-Trimethylcyclohexanone | $CH_2$=$CHCH_2NH_2$ | $ClCH_2$—$COCl$ |
| 64 | 2,2,4- und 2,4,4-Trimethylcyclopentanone(1:1) | $CH_2$=$CHCH_2NH_2$ | $ClCH_2$—$COCl$ |
| 65 | 3,5,5-Trimethylcyclohex-2-enone | $CH_2$=$CHCH_2NH_2$ | $ClCH_2$—$COCl$ |
| 66 | 3,3,5-Trimethylcyclohexanone | $CH_2$=$CHCH_2NH_2$ | $BrCH_2$—$COCl$ |

The following table summarizes the physical properties of the acetamides synthesized according to the preceding table.

| Example No. | Boiling point °C. | Refractive index $n_D^{20}$ | % N calc. | % N found | % Cl calc. | % Cl found | Molecular wt. calc. | Molecular wt. found | Amide bands IR (cm$^{-1}$) |
|---|---|---|---|---|---|---|---|---|---|
| 3 | 97–130 | — | 5,3 | 5,1 | 26,9 | 27,7 | 264,0 | 255 | 1650 |
| 4 | 80–120 | 1.5160 | — | — | 35,3 | 37,0 | 298,5 | 210 | — |
| 5 | — | 1.4679 | 5,9 | 4,6 | — | — | 237,0 | 205 | — |
| 6 | 105–120 | 1.4924 | 5,0 | 4,3 | 25,6 | 27,5 | 278,0 | 255 | 1625–45 |
| 7 | 87–92 | 1.4750 | 7,2 | 6,7 | — | — | 195,0 | 195 | 1630–50 |
| 8 | 87–110 | 1.4880 | 5,8 | 5,4 | 14,6 | 15,0 | 243,5 | 225 | 1650 |
| 9 | 120–140 | 1.4993 | 5,0 | 4,6 | 25,5 | 26,4 | 278,0 | 255 | 1650 |
| 10 | — | — | 4,5 | 4,7 | 34,1 | 34,6 | 312,5 | 280 | 1670 |
| 11 | 97–108 | 1.4750 | 5,6 | 5,1 | — | — | 251,0 | 240 | 1620 |
| 12 | 120–135 | 1.4888 | 4,8 | 4,1 | 24,3 | 25,3 | 292,0 | 260 | 1630 |
| 13 | 96–110 | 1.4746 | 6,7 | 5,9 | — | — | 209,0 | 195 | 1630–50 |
| 14 | — | — | 5,4 | 4,4 | 13,8 | 16,0 | 257,5 | 270 | 1650 |
| 15 | — | — | 4,8 | 4,9 | 24,3 | 19,4 | 292,0 | 285 | 1660 |
| 16 | — | 1.5300 | 4,3 | 3,9 | 32,6 | 34,1 | 326,5 | 300 | 1670 |
| 17 | 64–72 | 1.4539 | 5,3 | 6,5 | — | — | 265,0 | 270 | 1640 |
| 18 | — | — | 4,6 | 4,1 | 23,2 | 21,5 | 306,0 | 315 | 1640 |
| 19 | — | 1.4825 | 6,3 | 5,1 | — | — | 223,0 | 225 | 1630–50 |
| 20 | 108–120 | 1,4880 | 5,2 | 5,0 | 13,1 | 13,2 | 271,0 | 250 | 1650–70 |
| 21 | — | 1.5050 | 4,6 | 3,8 | 23,2 | 27,5 | 306,0 | 300 | 1660–1710 |
| 22 | — | 1.5040 | 4,1 | 3,8 | 31,3 | 30,9 | 340,5 | 335 | 1660–90 |
| 23 | 96–107 | 1.4723 | 5,0 | 4,7 | — | — | 279,0 | 270 | 1630 |
| 24 | 117–128 | 1.4895 | 4,4 | 3,8 | 22,2 | 26,2 | 320,0 | 300 | 1650 |
| 25 | 92–113 | 1.4680 | 5,9 | 6,3 | — | — | 237,0 | 215 | 1650 |
| 26 | 121–137 | 1.4994 | 5,6 | 5,5 | 28,4 | 29,5 | 250,0 | 235 | 1670 |
| 27 | 80–120 | 1.5215 | — | — | 37,1 | 35,0 | 284,5 | 247 | — |
| 28 | 84–90 | 1.4718 | 6,3 | 6,1 | — | — | 223,0 | 210 | 1625 |
| 29 | 87–99 | 1.4946 | 5,3 | 5,0 | 26,9 | 27,5 | 264,0 | 260 | 1660 |
| 30 | 74–90 | 1.4765 | 7,7 | 6,4 | — | — | 181.0 | 175 | 1620–40 |
| 31 | 108–125 | 1.4893 | 6,1 | 5,7 | 15,5 | 17.0 | 229,0 | 205 | 1660 |
| 32 | 110–132 | 1.5000 | 5,3 | 4,4 | 26,9 | 32,0 | 264,0 | 240 | 1690 |
| 33 | 110–125 | 1.5431 | 4,7 | 4,8 | 35,7 | 37,2 | 279,0 | 270 | 1655 |
| 34 | 87–98 | 1.4660 | 5,9 | 5,2 | — | — | 237,0 | 220 | 1620 |
| 35 | 80–103 | 1.4942 | 5,0 | 3,7 | 25,5 | 33,7 | 278,0 | 230 | 1640 |
| 36 | 87–120 | 1.4719 | 7,2 | 6,4 | — | — | 195,0 | 185 | 1650 |
| 37 | — | — | 5,7 | 4,6 | 14,6 | 17,9 | 243,0 | 230 | 1650 |
| 38 | 115–130 | 1.50 | 5,0 | 5,6 | 25,5 | 32,0 | 278,0 | 240 | 1665 |

-continued

| Example No. | Boiling point °C. | Refractive index $n_D^{20}$ | % N calc. | % N found | % Cl calc. | % Cl found | Molecular wt. calc. | Molecular wt. found | Amide bands IR (cm$^{-1}$) |
|---|---|---|---|---|---|---|---|---|---|
| 39 | — | — | 4,5 | 4,4 | 34,1 | 34,4 | 312,5 | 305 | 1665 |
| 40 | 68–79 | 1.4542 | 5,6 | 5,5 | — | | 251,0 | 200 | 1620 |
| 41 | — | — | 4,8 | 3,5 | 24,3 | 28,4 | 292,0 | 275 | 1645 |
| 42 | 86–110 | 1.4772 | 6,7 | 5,9 | — | | 209,0 | 215 | 1650 |
| 43 | 94–102 | 1.4835 | 5,4 | 6,6 | 13,8 | 16,1 | 257,5 | 190 | 1650–60 |
| 44 | 111–128 | 1.4900 | 4,9 | 5,4 | 24,7 | 25,7 | 292,0 | 235 | 1650–1700 |
| 45 | — | — | 4,3 | 4,3 | 32,6 | 31,5 | 326,5 | 300 | 1670 |
| 46 | 86–96 | 1.4675 | 5,3 | 5,0 | — | | 265,0 | 250 | 1630 |
| 47 | 94–106 | 1.5001 | 4,6 | 4,3 | 23,2 | 24,9 | 306,0 | 245 | 1650 |
| 48 | 87–98 | 1.4710 | 6,3 | 6,1 | — | | 223,0 | 215 | 1650 |
| 49 | 115–25 | 1.4883 | 5,2 | 5,1 | 13,1 | 13,8 | 271,5 | 250 | 1655 |
| 50 | 113–20 | 1.4870 | 5,4 | 5,6 | 13,8 | 13,9 | 257,5 | 190 | 1660 |
| 51 | 115–21 | 1.4909 | 5,1 | 5,0 | 13,0 | 13,2 | 273,5 | 280 | 1665 |
| 52 | 117–22 | 1.5105 | 5,2 | 4,9 | 13,1 | 13,6 | 271,5 | 260 | 1670 |
| 53 | — | — | 4,9 | 4,9 | 12,4 | 12,0 | 285,5 | 315 | 1670 |
| 54 | 110–40 | 1.4843 | 4,9 | 5,2 | 12,3 | 13,6 | 287,5 | 270 | 1650 |
| 55 | 113–18 | 1.4896 | 4,9 | 4,8 | 12,3 | 13,5 | 287,5 | 260 | 1655 |
| 56 | 120–29 | 1.4851 | 4,6 | 4,7 | 11,8 | 12,3 | 1.5122 | 260 | 1655 |
| 57 | — | 1,4840 | 4,2 | 4,3 | 10,8 | 11,1 | 329,5 | 290 | 1690 |
| 58 | 110–15 | 1.4983 | 5,1 | 5,8 | 29,2 | 36 | 273,9 | 210 | 1650 |
| 59 | 110–14 | 1.4990 | 4,9 | 5,5 | 27,8 | 32,3 | 287,9 | 230 | 1655 |
| 60 | 109–14 | 1.4889 | 4,4 | 4,9 | 25,3 | 30,2 | 315,9 | 245 | 1675 |
| 61 | 98–101 | 1.4980 | 5,4 | 5,6 | 30,7 | 37,5 | 259,9 | 210 | 1660 |
| 62 | — | 1.4970 | 4,4 | 5,3 | 25,1 | 29,6 | 317,9 | 270 | 1650 |
| 63 | 103–12 | 1.4974 | 5,5 | 5,4 | 13,9 | 14,8 | 255,5 | 230 | 1650 |
| 64 | 88–93 | 1.4978 | 5,8 | 6,1 | 14,7 | 15,9 | 241,5 | 210 | 1650 |
| 65 | 115–21 | 1.5122 | 5,5 | 4,8 | 14,0 | 16,3 | 253,3 | 210 | 1650 |

-continued

| Example No. | Boiling point °C. | Refractive index $n_D^{20}$ | % N calc. | % N found | % Cl calc. | % Cl found | Molecular wt. calc. | Molecular wt. found | Amide bands IR (cm$^{-1}$) |
|---|---|---|---|---|---|---|---|---|---|
| 66 | 105–10 | 1.4992 | 4,7 | 5,5 | 26,6 | 32,2 | 299,9 | 235 | 1690 |

Names of compounds 3–66:
3. N-(Trimethylclohexen-1-yl)-N-methyl-α-dichloroacetamide
4. N-(Trimethylcyclohexen-1-yl)-N-methylα-trichloroacetamide
5. N-(Trimethylcyclohexen-1-yl)-N-methylpivalamide
6. N-(Trimethylcyclohexen-1-yl)-N-methyl-α-dichloropropionamide
7. N-(Trimethylcyclohexen-1-yl)-N-methylacetamide
8. N-(Trimethylcyclohexen-1-yl)-N-ethyl-α-chloroacetamide
9. N-(Trimethylcyclohexen-1-yl)-N-ethyl-α-dichloroacetamide
10. N-(Trimethylcyclohexen-1-yl)-N-ethyl-α-trichloroacetamide
11. N-(Trimethylcyclohexen-1-yl)-N-ethylpivalamide
12. N-(Trimethylcyclohexen-1-yl)-N-ethyl-α-dichloropropionamide
13. N-(Trimethylcyclohexen-1-yl)-N-ethylacetamide
14. N-(Trimethylcyclohexen-1-yl)-N-isopropyl-α-chloroacetamide
15. N-(Trimethylcyclohexen-1-yl)-N-isopropyl-α-dichloroacetamide
16. N-(Trimethylcyclohexen-1-yl)-N-isopropyl-α-trichloroacetamide
17. N-(Trimethylcyclohexen-1-yl)-N-isopropylpivalamide
18. N-(Trimethylcyclohexen-1-yl)-N-isopropyl-α-dichloropropionamide
19. N-(Trimethylcyclohexen-1-yl)-N-isopropylacetamide
20. N-(Trimethylcyclohexen-1-yl)-N-isobutyl-α-chloroacetamide
21. N-(Trimethylcyclohexen-1-yl)-N-isobutyl-α-dichloroacetamide
22. N-(Trimethylcyclohexen-1-yl)-N-isobutyl-α-trichloroacetamide
23. N-(Trimethylcyclohexen-1-yl)-N-isobutylpivalamide
24. N-(Trimethylcyclohexen-1-yl)-N-isobutyl-α-dichloropropionamide
N-(Trimethylcyclohexen-1-yl)-N-isobutylacetamide
N-(Trimethylcyclogexen-1-yl)-N-isobutylacetamide
26. N-(Trimethylcyclopenten-1-yl)-N-methyl-α-dichloroacetamide
27. N-(Trimethylcyclopenten-1-yl)-N-methyl-α-trichloroacetmaide
28. N-(Trimethylcyclopenten-1-yl)-N-methylpivalamide
29. N-(Trimethylcyclopenten-1-yl)-N-methyl-α-dichloropropionamide
30. N-(Trimethylcyclopenten-1-yl)-N-methylacetamide
31. N-(Trimethylcyclopenten-1-yl)-N-ethylαchloroacetamide
32. N-(Trimethylcyclopenten-1-yl)-N-ethyl-α-dichloroacetamide
33. N-(Trimethylcyclopenten-1-yl)-N-ethyl-α-trichloroacetamide
34. N-(Trimethylcyclopenten-1-yl)-N-ethylpivalamide
35. N-(Trimethylcyclopenten-1-yl)-N-ethyl-α-dichloropropionamide
36. N-(Trimethylcyclopenten-1-yl)-N-ethylacetamide
37. N-(Trimethylcyclopenten-1-yl)-N-isopropyl-α-chloroacetamide
38. N-(Trimethylcyclopenten-1-yl)-N-isopropyl-α-dichloroacetamide
39. N-(Trimethylcyclopenten-1-yl)-N-isopropyl-α-trichloroacetamide
40. N-(Trimethylcyclopenten-1-yl)-N-isopropylpivalamide
41. N-(Trimethylcyclopenten-1-yl)-N-isopropyl-α-dichloropropionamide
42. N-(Trimethylcyclopenten-1-yl)-N-isopropylacetamide
43. N-(Trimethylcyclopenten-1-yl)-N-isobutyl-α-chloroacetamide
44. N-(Trimethylcyclopenten-1-yl)-N-isobutyl-α-dichloroacetamide
45. N-(Trimethylcyclopenten-1-yl)-N-isobutyl-α-trichloroacetamide
46. N-Trimethylcyclopenten-1-yl)-N-isobutylpivalamide
47. N-(Trimethylcyclopenten-1-yl)-N-isobutyl-α-dichloropropionamide
48. N-(Trimethylcyclopenten-1-yl)-N-isobutylacetamide
49. N-(Trimethylcyclopenten-1-yl)-N-butyl-α-chloracetamide
50. N-(Trimethylcyclopenten-1-yl)-N-butyl-α-chloracetamide
51. N-(Trimethylcyclohexen-1-yl)-N-methoxyethyl-α-chloroacetamide
52. N-(Trimethylcylcohexadien)-1-yl)-N-methoxyethyl-α-chloroacetamide
53. N-(Trimethylcyclohexadien-1-yl)-N-ethoxyethyl-α-chloroacetamide
54. N-(Trimethylcyclohexen-1-yl)-N-ethoxyethyl-α-chloroacetamide
55. N-(Trimethylcyclohexen-1-yl)-N-methoxypropyl-α-chloroacetamide
56. N-(Trimethylcyclohexen-1-yl)-N-ethoxypropyl-α-chloroacetamide
57. N-(Trimethylcyclohexen-1-yl)-N-butoxypropyl-α-chloroacetamide
58. N-(Trimethylcyclohexen-1-yl)-N-methyl-α-bromoacetamide
59. N-(Trimethylcyclohexen-1-yl)-N-ethyl-α-bromoacetamide
60. N-(Trimethylcyclohexen-1-yl)-N-isobutyl-α-bromoacetamide
61. N-(Trimethylcyclopenten-1-yl)-N-methyl-α-bromoacetamide
62. N-(Trimethylcyclohexen-1-yl)-N-methoxyethyl-α-bromoacetamide
63. N-(Trimethylcyclohexen-1-yl)-N-allyl-α-chloroacetamide
64. N-(Trimethylcyclopenten-1-yl)-N-allyl-α-chloroacetamide
65. N-(Trimethylcyclohexadien-1-yl)-N-allyl-α-chloroacetamide
66. N-(Trimethylcyclohexen-1-yl)-N-allyl-α-bromoacetamide The process of using the herbicidal compounds of the invention to selectively treat agricultural crops is characterized by using for the crop treatment, before and/or after the emergence of the young crop plants, a compound of formula I. The active material can be applied to the crops in an amount of 0.5 to 10 kilograms per 10,000 square meters, preferably 2–5 kilograms per 10,000 square meters.

The compounds of formula I are herbicides which, among other things, exhibit the pre-emergent application a broad-spectrum selectivity with respect to crops and a very great effect on grasses and monocotyledonous weeds. In post-emergent application also great effectiveness can be obtained. The N-(trimethylcycloalkenyl)-N-alkylacetamides of the invention are selective with respect to, among others, dicotyledonous crops such as turnips (*Brassica rapa*), sugar beets (*Beta vulgaris*), soybeans (*Soya hispida*), and cotton. They also possess selectivity with respect to the monocotyledonous crop maize (*Zea mays*). The broad-spectrum effectiveness of the compounds of the invention against grasses such as barnyard grass (*Echinocloa crusgalli*), hairy crabgrass (*Digitaria sanguinalis*), green foxtail (*Setaria viridis*), crabgrass (*Digitaria ischaemum*) and field foxtail (*Alopecurus myosoroides*) as well as certain dicotyledonous weeds, such as camomile (*Anthemis* spec.), chickweed (*Stellaria media*), wild beet (*Amaranthus retroflexus*), dead nettle (*lamium purpureum*) and white goosefoot (*Chenopodium album*) makes the compounds very useful in the cultivation of a number of crops such as turnips (*Brassica rapa*), maize (*Zea mays*) and sugar beets (*Beta vulgaris*).

The compounds of the invention are effective to a satisfactory degree when applied in amounts of 0.5 kilogram per 10,000 square meters or more, calculated as the pure active ingredient, and, in spite of their broad-spectrum activity, can be applied to the above-mentioned crops without visible damage to the plants. This extraordinary crop compatibility is an important advance in the art, since it is well known that many of the known herbicides only exert a sufficient biological activity against weeds when the toxic threshhold for the crops has been slightly exceeded.

For various types of grain, for example, winter barley, the N-(trimethylcycloalkenyl)-N-alkylacetamides have an inhibiting effect on the height, without, however, causing a decreased yield; accordingly, they can also be applied as growth regulators. It is a great additional advantage of the compounds of the invention that no aromatic groups are present in the molecule. This automatically eliminates the aromatically bonded halogen which is contained in many herbicides and presents very great ecological problems because of residues.

Inhibition of photosynthesis by the new compounds also takes place, especially when they are present only in small amounts. Certain of the new compounds also exhibit fungicidal activity.

Especially advantageous for use in growing turnips, beets, soybeans, cotton and maize are those agents having the six-membered ring of formula I wherein $X_3$ are chlorine or bromine in combination with two hydrogens in each case, R is a linear or branched saturated alkyl radical having 1 to 4 carbon atoms, and the three methyl groups are arranged in the 3,3,5- or 3,5,5-positions.

The greatest activity is found when $X_3$ signifies chlorine and two hydrogens and R is methyl. In this case, complete compatibility is found at 3–4 kilograms per hectare for corn, beets, soybeans, cotton, and turnips in dose-activity testing. This clearly surpasses in versatility the known herbicides tested as comparative materials.

Other comparable cyclic ketones of formula 2 yield a lower degree of activity.

The compounds of the invention or their mixtures are advantageously applied in mixtures with at least one adjuvant selected from the group consisting of carriers, diluents, wetting agents, dispersants, and emulsifiers, wherein the last three are also characterized as conditioning agents.

In order to simplify the following discussion, the term "agent" will be used in place of the expression N-(cycloalkenyl)-N-alkylacetamide.

The herbicidal compositions of this invention contain at least one agent and at least one adjuvant in liquid, paste, or solid form. The compositions can be prepared by mixing the agents with at least one adjuvant, including diluents, fillers, carriers, and conditioning agents to make a composition in the form of finely divided particulate solids, granules, pellets, solutions, dispersions or emulsions. Consequently, the agent can be used with an adjuvant such as a finely divided solid, a liquid of organic origin, water, a wetting agent, a dispersant, an emulsifier, or any suitable combination of these agents.

Typical finely divided carriers and fillers for the plant growth regulators of this invention can include, for example, talc, clays, pumice, silicon dioxide (quartz), silicic acid, diatomaceous earth, chalk, walnut meal, fuller's earth, salt, sulfur, pulverized cork, pulverized wood, charcoal, ground corncobs, illite clay, tobacco dust, volcanic ash, cottonseed meal, wheat flour, soybean meal, tripoli, and the like.

Typical liquid diluents are water, kerosine, diesel oil, hexane, ketones such as acetone, toluene, benzene, xylene, tetrahydronaphthalene and aromatic fractions generally, alcohols, glycols, ethylene dichloride, and the like.

The herbicidal compositions of this invention, especially the liquids and wettable powders, generally also contain as conditioning agents one or more surfactants in amounts to make the compositions easily dispersible in water or oil.

The term "surfactant" includes wetting agents, dispersants, suspending agents and emulsifiers without restriction.

The term "herbicidal composition" as used here, signifies not only compositions in a form suitable for application, but also concentrates which have to be thinned or extended with a suitable quantity of liquid or solid adjuvant before application.

The agents can be applied alone or in combination with other types of agents. Thus, other herbicidal materials such as chlorinated phenoxycarboxylic acids, substituted ureas, triazines, carbamates and others, or materials with fungicidal activity such as derivatives of thiocarbonic acid, thiocarbamates, isothiocyanates, carboxylic acid imides, or materials with insecticidal activity such as chlorinated hydrocarbons and phosphoric acid esters, can be added to the desired combination in order to obtain special effects or to extend its already broad-spectrum activity even further.

The following examples illustrate the preparation of the agents for a practical application, their application, as well as the activity attained.

As comparison substances, besides the known commercial products such as atrazine, diallate, pyrazone, dimethachlor, and trifluoraline, the following compounds were also used: N,N-diallylchloroacetamide according to U.S. Pat. No. 2,864,683, N-(isopropyl-2-methylpropen-1-yl)-N-methoxyethylchloroacetamide according to German Offenlegungsschrift No. 25 26 868, N-(trimethylcyclohexadien-1-yl)-N-ethoxyethylchloroacetamide according to German Offenlegungsschrift No. 20 45 380, N-benzyl-N-isopropyltrimethylacetamide according to U.S. Pat. No. 3,707,366, and N-(2,6-dimethylphenyl)-N-methoxyethyl-α-chloroacetamide according to German Offenlegungsschrift No. 23 05 495.

EXAMPLE 6

Preparation of the emulsion concentrate (a) 20 parts by weight of the compound of Example 1 were mixed with 180 parts by weight of xylene (technical mixture) and 20 parts by weight of an emulsifier which was a mixture of anionic and nonionic surfactants and is commercially available under the name MULSIFAN ® RT 18. The emulsion concentrate was then diluted with water before application to the appropriate concentration for use.

(b) 600 parts by weight of agent according to Example 1 were mixed with the same emulsifiers as in Example (a) without additional solvent to prepare an emulsion concentrate ready for use. At relatively low temperatures the agent can crystallize out. However, by gently warming the mixture a homogeneous emulsion concentrate can again be obtained which is completely equivalent in its properties to the original concentrate.

Application of the agent

In a greenhouse test the compounds of the invention listed in Table I, in an amount of 1–4 kilograms per 10,000 square meters, calculated as the pure agent, were suspended in 1200 liters of water per 10,000 square meters, and applied to the test plants listed in Table I in a pre-emergent test. The materials were applied to the surface of the soil before germination of the seed.

The following agents were applied for comparison:

Comparison (a): N-(isopropyl-2-methylpropene-1-yl)-N-methoxyethylchloroacetamide according to German Offenlegungsschrift No. 25 26 868.

Comparison (b): N-benzyl-N-isopropyltrimethylacetamide according to U.S. Pat. No. 3,707,366.
Trade name: BUTAM ®

Comparison (c): N-(2,6-dimethylphenyl)-N-methoxyethyl-α-chloroacetamide according to German Offenlegungsschrift No. 23 05 495.
Trade name: TERIDOX ®

Comparison (d): N,N-diallylchloroacetamide according to U.S. Pat. No. 2,864,863.
Trade name: RANDOX ®

Comparison (e): N-(2,6-diethylphenyl)-N-methoxymethylchloroacetamide.
Trade name: LASSO ®

Table II presents selected examples which make clear the great effectiveness of the substances of this invention, even when used in small amounts, in comparison with the usual commercial products.

TABLE I

| | Example 1 | | | | Example 2 | | | | Example 8 | | | | Example 14 | | | | Example 20 | | | |
|---|---|---|---|---|---|---|---|---|---|---|---|---|---|---|---|---|---|---|---|---|
| Amount applied kg/ha | 1 | 2 | 3 | 4 | 1 | 2 | 3 | 4 | 1 | 2 | 3 | 4 | 1 | 2 | 3 | 4 | 1 | 2 | 3 | 4 |
| Test plant | | | | | | | | | | | | | | | | | | | | |
| White mustard | 5 | 5 | 4 | 4 | 5 | 5 | 5 | 5 | 5 | 5 | 4.5 | 4 | | | | | 5 | 5 | 5 | 5 |
| Tomato | 4 | 3 | 3 | 2 | 5 | 5 | 5 | 5 | 5 | 5 | 4.5 | 4 | | | | | 5 | 5 | 5 | 5 |
| Oats | 4 | 4 | 3 | 3 | 5 | 5 | 5 | 4 | 4 | 3 | 2.5 | 2 | 4 | 3 | 2 | 2 | 5 | 5 | 5 | 5 |
| Barnyard grass | 1 | 1 | 1 | 1 | 1 | 1 | 1 | 1 | 1 | 1 | 1 | 1 | 1 | 1 | 1 | 1 | 1 | 1 | 1 | 1 |
| Wild oats | 3 | 2 | 1.5 | 1.5 | 5 | 5 | 5 | 5 | 1.5 | 1 | 1 | 1 | 3 | 2 | 1 | 1 | 3 | 5 | 5 | 5 |
| Field foxtail | 1 | 1 | 1 | 1 | 1 | 1 | 1 | 1 | 1 | 1 | 1 | 1 | 1 | 1 | 1 | 1 | 2 | 2 | 1 | 1 |
| Chickweed | 3 | 2 | 1.5 | 1.5 | 5 | 5 | 4 | 4 | 4 | 4 | 3 | 2 | 2 | 1 | 1 | 1 | | | | 5 |
| Bedstraw | 4 | 4 | 4 | 2 | 4 | 2.5 | 1.5 | 1.5 | 2 | 1 | 1 | 1 | 4 | 3 | 2 | 2 | | | | 5 |
| Cornflower | 5 | 5 | 5 | 4 | 5 | 5 | 5 | 4 | 4 | 3 | 2.5 | 2.5 | 5 | 5 | 5 | 5 | 5 | 5 | 5 | 5 |
| Camomile | 1 | 1 | 1 | 1 | 5 | 5 | 5 | 5 | 1.5 | 1 | 1 | 1 | 3 | 1.5 | 1 | 1 | 5 | 4 | 4 | 4 |
| Dead nettle | 1 | 1 | 1 | 1 | 3 | 2 | 2 | 1.5 | 1 | 1 | 1 | 1 | 1 | 1 | 1 | 1 | 4 | 3 | 3 | 2 |
| Hemp nettle | 2 | 1 | 1 | 1 | 2.5 | 2 | 1.5 | 1.5 | 1.5 | 1 | 1 | 1 | 1.5 | 1.5 | 1 | 1 | 5 | 4 | 4 | 2.5 |
| Wild beet | 2 | 1.5 | 1.5 | 1.5 | 5 | 5 | 4 | 4 | 2 | 1.5 | 1 | 1 | 1 | 1 | 1 | 1 | | | | 5 |
| White goosefoot | 1.5 | 1 | 1 | 1 | 4 | 3 | 3 | 3 | 3 | 1.5 | 1 | 1 | 1.5 | 1 | 1 | 1 | 5 | 4 | 4 | 3 |
| Vetch | 2.5 | 2 | 1 | 1 | 5 | 5 | 4 | 4 | 1.5 | 1 | 1 | 1 | 4 | 3 | 3 | 2.5 | 5 | 5 | 4 | 4 |
| Sugar beet | 5 | 5 | 5 | 5 | 5 | 5 | 4 | 3.5 | 4.5 | 4 | 2 | 2 | 5 | 4 | 4 | 4 | 5 | 5 | 5 | 5 |
| Turnip | 5 | 5 | 5 | 5 | 5 | 5 | 5 | 5 | 5 | 5 | 5 | 5 | 5 | 5 | 5 | 5 | 5 | 5 | 5 | 5 |
| Knot grass | 5 | 5 | 4 | 2.5 | 5 | 5 | 5 | 5 | 4.5 | 3 | 2 | 1.5 | 5 | 4 | 4 | 4 | 5 | 5 | 4 | 3.5 |
| Maize | 5 | 5 | 4 | 4 | 5 | 5 | 5 | 5 | 5 | 4.5 | 4 | 3.5 | | | | | 5 | 5 | 5 | 5 |
| Corn poppy | 1.5 | 1 | 1 | 1 | 4 | 4 | 3 | 3 | 1 | 1 | 1 | 1 | 1.5 | 1 | 1 | 1 | 5 | 5 | 4 | 2 |

| | Example 31 | | | | Example 37 | | | | Example 51 | | | | Example 63 | | | | Example 64 | | | |
|---|---|---|---|---|---|---|---|---|---|---|---|---|---|---|---|---|---|---|---|---|
| Amount applied kg/ha | 1 | 2 | 3 | 4 | 1 | 2 | 3 | 4 | 1 | 2 | 3 | 4 | 1 | 2 | 3 | 4 | 1 | 2 | 3 | 4 |
| Test plant | | | | | | | | | | | | | | | | | | | | |
| White mustard | 5 | 5 | 5 | 5 | | | | 5 | 5 | 5 | 4 | 4 | 5 | 5 | 4 | 4 | 5 | 5 | 4 | 4 |
| Tomato | 5 | 4 | 2 | 2 | | | | 4 | 5 | 5 | 4 | 3 | 3.5 | 2 | 2 | 1.5 | 5 | 4 | 4 | 2.5 |
| Oats | 4 | 3 | 2 | 1 | 5 | 5 | 4 | 4 | 4 | 3 | 3 | 2 | 1.5 | 1 | 1 | 1 | 5 | 5 | 4.5 | 4 |
| Barnyard grass | 1 | 1 | 1 | 1 | 1 | 1 | 1 | 1 | 1 | 1 | 1 | 1 | 1 | 1 | 1 | 1 | 1 | 1 | 1 | 1 |
| Wild oats | 3 | 3 | 2 | 1 | 4 | 4 | 3 | 2 | 2 | 1.5 | 1 | 1 | 1 | 1 | 1 | 1 | 4 | 2 | 2 | 1.5 |
| Field foxtail | 1 | 1 | 1 | 1 | 3 | 2 | 2 | 1 | 1 | 1 | 1 | 1 | 1 | 1 | 1 | 1 | 1 | 1 | 1 | 1 |
| Chickweed | 3 | 2.5 | 2 | 1 | 2.5 | 2 | 1 | 1 | 5 | 3 | 2.5 | 1.5 | 1.5 | 1 | 1 | 1 | 3.5 | 3.5 | 3 | 2.5 |
| Bedstraw | 5 | 4 | 4 | 3.5 | 5 | 4.5 | 4.5 | 3 | 3 | 2 | 1.5 | 1.5 | 2 | 2 | 1.5 | 1.5 | 4 | 4 | 3 | 3 |
| Cornflower | 5 | 5 | 5 | 4 | 5 | 5 | 4 | 4 | 4 | 4 | 4 | 4 | 4 | 3.5 | 3 | 3 | 5 | 5 | 4 | 4 |
| Camomile | 4 | 4 | 2 | 1.5 | 5 | 5 | 4 | 3 | 2 | 1 | 1 | 1 | 1 | 1 | 1 | 1 | 1.5 | 1 | 1 | 1 |
| Dead nettle | 2 | 1.5 | 1 | 1 | 2 | 2 | 1 | 1 | 2 | 2 | 1 | 1 | 1 | 1 | 1 | 1 | 2 | 1 | 1 | 1 |
| Hemp nettle | 3.5 | 3 | 2 | 2 | 5 | 4 | 4 | 2.5 | 1 | 1 | 1 | 1 | 1.5 | 1 | 1 | 1 | 1.5 | 1.5 | 1.5 | 1 |
| Wild beet | 2 | 1 | 1 | 1 | 1 | 1 | 1 | 1 | 4 | 3 | 2 | 1.5 | 3.5 | 2 | 1.5 | 1.5 | 4 | 4 | 3 | 2 |
| White goosefoot | 2 | 1.5 | 1 | 1 | 3 | 2 | 1.5 | 1 | 1 | 1 | 1 | 1 | 1 | 1 | 1 | 1 | 2.5 | 2 | 1.5 | 1.5 |
| Vetch | 5 | 5 | 5 | 4 | 5 | 4 | 4 | 3 | 1 | 1 | 1 | 1 | 1 | 1 | 1 | 1 | 2 | 2 | 2 | 1.5 |
| Sugar beet | 5 | 5 | 4 | 4 | 5 | 4 | 4 | 4 | 5 | 4 | 4 | 3 | 4 | 3 | 3 | 2.5 | 5 | 4 | 3.5 | 3.5 |
| Turnip | 5 | 5 | 5 | 5 | 5 | 5 | 5 | 5 | 5 | 5 | 5 | 5 | 5 | 5 | 5 | 5 | 5 | 5 | 5 | 5 |
| Knot grass | 5 | 5 | 5 | 5 | 5 | 5 | 5 | 5 | 3 | 2 | 2 | 2 | 3.5 | 2 | 2 | 1.5 | 4 | 4 | 3.5 | 3.5 |
| Maize | 4 | 3.5 | 3.5 | 3 | 4 | 4 | 4 | 4 | 4 | 4 | 3.5 | 3 | 4 | 4 | 4 | 4 | 5 | 5 | 5 | 5 |
| Corn poppy | 3 | 3 | 2 | 2 | 5 | 5 | 4 | 2 | | | | | 5 | 4 | 3 | 2 | | | | |

| | Example 65 | | | | Comparison a | | | | Comparison b | | | | Comparison c | | | | Comparison d | | | |
|---|---|---|---|---|---|---|---|---|---|---|---|---|---|---|---|---|---|---|---|---|
| Amount applied kg/ha | 1 | 2 | 3 | 4 | 1 | 2 | 3 | 4 | 1 | 2 | 3 | 4 | 1 | 2 | 3 | 4 | 1 | 2 | 3 | 4 |
| Test plant | | | | | | | | | | | | | | | | | | | | |
| White mustard | 5 | 5 | 5 | 5 | 5 | 4.5 | 4 | 2.5 | 5 | 5 | 5 | 4 | 4 | 3 | 2 | 1.5 | | | | |
| Tomato | 5 | 5 | 4 | 4 | 5 | 4.5 | 3.5 | 2 | 5 | 4 | 4 | 3.5 | 1.5 | 1 | 1 | 1 | | | | |
| Oats | 5 | 5 | 4 | 4 | 5 | 4 | 4 | 3 | 3 | 1 | 1 | 1 | 1.5 | 1 | 1 | 1 | 4 | 3 | 2 | 2 |
| Barnyard grass | 1 | 1 | 1 | 1 | 1 | 1 | 1 | 1 | 1 | 1 | 1 | 1 | 1 | 1 | 1 | 1 | 1 | 1 | 1 | 1 |

TABLE I-continued

| Test plant | | | | | | | | | | | | | | | | | | | | |
|---|---|---|---|---|---|---|---|---|---|---|---|---|---|---|---|---|---|---|---|---|
| Wild oats | 3 | 2 | 2 | 1.5 | 4 | 3 | 1.5 | 1 | 2 | 1 | 1 | 1 | 1.5 | 1 | 1 | 1.5 | 4 | 2 | 2 | 2 |
| Field foxtail | 1 | 1 | 1 | 1 | 2 | 1.5 | 1 | 1 | 1 | 1 | 1 | 1 | 1 | 1 | 1 | 1 | 2.5 | 2 | 1 | 1 |
| Chickweed | 5 | 5 | 3.5 | 3 | 4 | 2 | 1 | 1 | 2.5 | 2 | 2 | 2 | 1 | 1 | 1 | 1 | 3 | 2 | 2 | 2 |
| Bedstraw | 5 | 4 | 3 | 3 | 2 | 1.5 | 1 | 1 | 4 | 4 | 3.5 | 3 | 1.5 | 1.5 | 1 | 1 | 5 | 5 | 4 | 4 |
| Cornflower | 5 | 5 | 5 | 5 | 5 | 4 | 3 | 2 | 5 | 5 | 5 | 4 | 5 | 4 | 4 | 2.5 | 5 | 5 | 4 | 3.5 |
| Camomile | 2.5 | 2.5 | 1 | 1 | 1 | 1 | 1 | 1 | 2 | 1.5 | 1 | 1 | 1 | 1 | 1 | 1 | 3 | 3 | 2 | 2 |
| Dead nettle | 2 | 2 | 2 | 2 | 1 | 1 | 1 | 1 | 2 | 1.5 | 1 | 1 | 2 | 1 | 1 | 1 | 2 | 1 | 1 | 1 |
| Hemp nettle | 2.5 | 2 | 2 | 1.5 | | | | | 2 | 2 | 1.5 | 1.5 | 1 | 1 | 1 | 1 | 5 | 5 | 4 | 4 |
| Wild beet | 5 | 5 | 4 | 4 | 1.5 | 1 | 1 | 1 | 5 | 4 | 4 | 3 | 1 | 1 | 1 | 1 | 2 | 2 | 2 | 1.5 |
| White goosefoot | 5 | 4 | 4 | 3 | 1.5 | 1 | 1 | 1 | 2 | 2 | 1.5 | 1.5 | 1.5 | 1 | 1 | 1 | 3 | 2 | 2 | 2 |
| Vetch | 3 | 2 | 2 | 2 | | | | | 2.5 | 1.5 | 1.5 | 1.5 | 2 | 1.5 | 1 | 1 | 5 | 4 | 4 | 3 |
| Sugar beet | 5 | 5 | 4 | 4 | 4 | 2.5 | 1.5 | 1.5 | 4 | 4 | 3.5 | 3.5 | | | | | 4 | 3.5 | 3 | 2 |
| Turnip | 5 | 5 | 5 | 5 | 4.5 | 4 | 2.5 | 2 | 5 | 5 | 5 | 4.5 | 5 | 5 | 5 | 4 | 5 | 5 | 5 | 5 |
| Knot grass | 5 | 4 | 4 | 4 | 3.5 | 2 | 1.5 | 1.5 | 4 | 3 | 2.5 | 1.5 | 1.5 | 1 | 1 | 5 | 5 | 5 | 4 | |
| Maize | 5 | 5 | 5 | 5 | 4 | 4 | 3 | 3 | 5 | 5 | 4 | 4 | 1 | 1 | 1 | 1 | 5 | 5 | 5 | 4 |
| Corn poppy | | | | | 4 | 3 | 2 | 2 | 4 | 3 | 3 | 2 | | | | | 5 | 5 | 4 | 4 |

| | Example | | | | | | | | | | | | | | | | | | | |
|---|---|---|---|---|---|---|---|---|---|---|---|---|---|---|---|---|---|---|---|---|
| | 1 | | | | 2 | | | | 8 | | | | 14 | | | | 20 | | | |
| Amount applied kg/ha | 1 | 2 | 3 | 4 | 1 | 2 | 3 | 4 | 1 | 2 | 3 | 4 | 1 | 2 | 2 | 4 | 1 | 2 | 3 | 4 |
| Test plant | | | | | | | | | | | | | | | | | | | | |
| Pansy | 3 | 3 | 2.5 | 2 | 5 | 5 | 5 | 5 | 4 | 4 | 3 | 2.5 | 5 | 5 | 4 | 4 | 5 | 5 | 4 | 4 |
| Green foxtail | 1 | 1 | 1 | 1 | 1 | 1 | 1 | 1 | 1 | 1 | 1 | 1 | 1 | 1 | 1 | 1 | 1 | 1 | 1 | 1 |
| Hairy crabgrass | 1 | 1 | 1 | 1 | 1 | 1 | 1 | 1 | 1 | 1 | 1 | 1 | 1 | 1 | 1 | 1 | 1 | 1 | 1 | 1 |
| Crabgrass | 1 | 1 | 1 | 1 | 1 | 1 | 1 | 1 | 1 | 1 | 1 | 1 | 1 | 1 | 1 | 1 | 1.5 | 1 | 1 | 1 |
| Spring barley | 3 | 3 | 2.5 | 2 | 5 | 5 | 4 | 4 | 4 | 3 | 3 | 2 | | | | | 5 | 5 | 5 | 5 |
| Spring wheat | 3 | 3 | 3 | 3 | 4 | 4 | 4 | 4 | 3 | 2 | 2 | 1.5 | | | | | 5 | 5 | 5 | 5 |
| Bent grass | 1 | 1 | 1 | 1 | 1 | 1 | 1 | 1 | 1 | 1 | 1 | 1 | 1 | 1 | 1 | 1 | 2 | 1 | 1 | 1 |
| Soybean | 4 | 3 | 1 | 1 | 5 | 5 | 5 | 4 | 5 | 5 | 4 | 4 | 5 | 5 | 5 | 4.5 | 5 | 5 | 4.5 | 4 |
| Winter barley | 4 | 4 | 3 | 3 | 4 | 4 | 4 | 4 | 4 | 3.5 | 2.5 | 2.5 | 4 | 3 | 3 | 2 | 5 | 5 | 5 | 5 |
| Winter wheat | 4 | 3 | 3 | 3 | 5 | 5 | 5 | 4 | 2.5 | 2 | 2 | 1.5 | 3 | 2 | 2 | 2 | 5 | 5 | 5 | 5 |
| Rye | 4 | 4 | 3 | 2.5 | | | | | | | | | | | | | | | | |
| Quack grass | 5 | 5 | 4 | 4 | 4.5 | 4 | 4 | 4 | 4 | 3 | 2.5 | 2 | 4 | 4 | 3 | 3 | 5 | 5 | 4 | 4 |

| | Example | | | | | | | | | | | | | | | | | | | |
|---|---|---|---|---|---|---|---|---|---|---|---|---|---|---|---|---|---|---|---|---|
| | 31 | | | | 37 | | | | 51 | | | | 63 | | | | 64 | | | |
| Amount applied kg/ha | 1 | 2 | 3 | 4 | 1 | 2 | 3 | 4 | 1 | 2 | 3 | 4 | 1 | 2 | 3 | 4 | 1 | 2 | 3 | 4 |
| Test Plant | | | | | | | | | | | | | | | | | | | | |
| Pansy | 5 | 4.5 | 4 | 4 | 5 | 5 | 5 | 4 | | | | | 5 | 4 | 4 | 4 | | | | |
| Green foxtail | 1 | 1 | 1 | 1 | 1 | 1 | 1 | 1 | 1 | 1 | 1 | 1 | 1 | 1 | 1 | 1 | 1 | 1 | 1 | 1 |
| Hairy crabgrass | 1 | 1 | 1 | 1 | 1 | 1 | 1 | 1 | 1 | 1 | 1 | 1 | 1 | 1 | 1 | 1 | 1 | 1 | 1 | 1 |
| Crabgrass | 1 | 1 | 1 | 1 | 1 | 1 | 1 | 1 | 1 | 1 | 1 | 1 | 1 | 1 | 1 | 1 | 1 | 1 | 1 | 1 |
| Spring barley | | | | | | | | | 4 | 3 | 2.5 | 2.5 | 4.5 | 2 | 1.5 | 1.5 | 2 | 2 | 1.5 | 1 |
| Spring wheat | | | | | | | | | 3.5 | 3 | 2 | 1.5 | 3 | 1.5 | 1 | 1 | 2 | 1.5 | 1.5 | 1 |
| Bent grass | 1 | 1 | 1 | 1 | 1 | 1 | 1 | 1 | 1 | 1 | 1 | 1 | 1 | 1 | 1 | 1 | 1 | 1 | 1 | 1 |
| Soybean | 5 | 5 | 4 | 4 | 5 | 5 | 5 | 5 | 5 | 5 | 5 | 5 | 5 | 4 | 4 | 4 | 5 | 5 | 5 | 4 |
| Winter barley | 2 | 1 | 1 | 1 | 4 | 4 | 3 | 2 | 4 | 2 | 1.5 | 1 | 2.5 | 1.5 | 1 | 1 | 2.5 | 1.5 | 1.5 | 1 |
| Winter wheat | 2 | 2 | 1 | 1 | 3 | 3 | 1.5 | 1 | 2.5 | 2 | 2 | 1.5 | 2 | 1.5 | 1 | 1 | 2 | 1.5 | 1 | 1 |
| Rye | | | | | | | | | 1.5 | 1.5 | 1 | 1 | 1.5 | 1 | 1 | 1 | 1.5 | 1 | 1 | 1 |
| Quack grass | 5 | 4 | 2.5 | 2 | 5 | 5 | 4.5 | 4 | | | | | 5 | 5 | 4 | 4 | | | | |

| | Example | | | | | | | | | | | | | | | | | | | |
|---|---|---|---|---|---|---|---|---|---|---|---|---|---|---|---|---|---|---|---|---|
| | 65 | | | | Comparison a | | | | Comparison b | | | | Comparison c | | | | Comparison d | | | |
| Amount applied kg/ha | 1 | 2 | 3 | 4 | 1 | 2 | 3 | 4 | 1 | 2 | 3 | 4 | 1 | 2 | 3 | 4 | 1 | 2 | 3 | 4 |
| Test plant | | | | | | | | | | | | | | | | | | | | |
| Pansy | | | | | 4.5 | 4 | 3.5 | 3 | 3 | 3 | 2.5 | 2.5 | | | | | 5 | 5 | 5 | 4 |
| Green foxtail | 1 | 1 | 1 | 1 | 1 | 1 | 1 | 1 | 1 | 1 | 1 | 1 | 1 | 1 | 1 | 1 | 1 | 1 | 1 | 1 |
| Hairy crabgrass | 1 | 1 | 1 | 1 | 1 | 1 | 1 | 1 | 1 | 1 | 1 | 1 | 1 | 1 | 1 | 1 | 1.5 | 1 | 1 | 1 |
| Crabgrass | 1 | 1 | 1 | 1 | 1 | 1 | 1 | 1 | 1 | 1 | 1 | 1 | 1 | 1 | 1 | 1 | 1.5 | 1 | 1 | 1 |
| Spring barley | 5 | 4 | 3 | 2.5 | 4 | 3.5 | 2 | 1 | 4 | 2 | 1 | 1 | 4 | 2 | 1 | 1 | | | | |
| Spring wheat | 4 | 3 | 2 | 2 | 2.5 | 2 | 2 | 1.5 | 3 | 1.5 | 1 | 1 | 1.5 | 1 | 1 | 1 | | | | |
| Bent grass | 1 | 1 | 1 | 1 | 1 | 1 | 1 | 1 | 1 | 1 | 1 | 1 | 1 | 1 | 1 | 1 | | | | |
| Soybean | 5 | 5 | 5 | 5 | 4 | 3 | 2 | 2 | 4 | 4 | 4 | 4 | 4 | 3 | 2 | 2 | 4 | 4 | 3.5 | 3.5 |
| Winter barley | 5 | 4 | 3.5 | 3.5 | | | | | 2.5 | 1 | 1 | 1 | 1.5 | 1.5 | 1 | 1 | 5 | 4.5 | 4 | 4 |
| Winter wheat | 2.5 | 2 | 1.5 | 1 | 4.5 | 4 | 3 | 2 | 3 | 1.5 | 1 | 1 | 2 | 1.5 | 1 | 1 | 4 | 4 | 3.5 | 3.5 |
| Rye | 1.5 | 1.5 | 1 | 1 | 5 | 4 | 3.5 | 3 | 1 | 1 | 1 | 1 | 1 | 1 | 1 | 1 | | | | |
| Quack grass | | | | | | | | | 2 | 2 | 1.5 | 1.5 | | | | | 4.5 | 3.5 | 2 | 1.5 |

1 = completely effective; plant killed
5 = no effect; plant appears as if untreated

TABLE II

| | Example | | | | | | | | | | | | | | | | | | | |
|---|---|---|---|---|---|---|---|---|---|---|---|---|---|---|---|---|---|---|---|---|
| | 8 | | | | 14 | | | | 66 | | | | Comparison e | | | | Comparison d | | | |
| Amount applied kg/ha | 0.063 | 0.125 | 0.25 | 0.5 | 0.063 | 0.125 | 0.25 | 0.5 | 0.063 | 0.125 | 0.25 | 0.5 | 0.063 | 0.125 | 0.25 | 0.5 | 0.063 | 0.125 | 0.25 | 0.5 |
| Test plant | | | | | | | | | | | | | | | | | | | | |
| Green foxtail | 1 | 1 | 1 | 1 | 1 | 1 | 1 | 1 | 1 | 1 | 1 | 1 | 3 | 2 | 1 | 1 | 3 | 1.5 | 1.5 | 1 |
| Hairy crabgrass | 1 | 1 | 1 | 1 | 1 | 1 | 1 | 1 | 1.5 | 1 | 1 | 1 | 4 | 3 | 1 | 1 | 4 | 4 | 3 | 1.5 |

TABLE II-continued

| Amount applied kg/ha | 8 | | | | 14 | | | | 66 | | | | Comparison e | | | | Comparison d | | | |
|---|---|---|---|---|---|---|---|---|---|---|---|---|---|---|---|---|---|---|---|---|
| | 0.063 | 0.125 | 0.25 | 0.5 | 0.063 | 0.125 | 0.25 | 0.5 | 0.063 | 0.125 | 0.25 | 0.5 | 0.063 | 0.125 | 0.25 | 0.5 | 0.063 | 0.125 | 0.25 | 0.5 |
| Crabgrass | 1 | 1 | 1 | 1 | 1 | 1 | 1 | 1 | 1 | 1 | 1 | 1 | 2 | 2 | 2 | 1 | 4 | 4 | 2 | 1.5 |
| Barnyard grass | 1 | 1 | 1 | 1 | 1 | 1 | 1 | 1 | 1.5 | 1 | 1 | 1 | 4 | 2 | 1 | 1 | 5 | 4 | 4 | 1.5 |
| Field foxtail | 2 | 1 | 1 | 1 | 2 | 1 | 1 | 1 | 3.5 | 2 | 1 | 1 | 4 | 4 | 1.5 | 1 | 5 | 4 | 3.5 | 3.5 |
| Chickweed | | | 2 | 2 | | | 2 | 2 | 2 | 1.5 | 1.5 | 1.5 | | | 2 | 2 | | | 4 | 2 |
| Cornflower | | | 4 | 4 | | | 5 | 4 | | | | | | | | | | | 5 | 5 |
| Camomile | | | 2 | 2 | | | 2 | 2 | 5 | 4 | 4 | 4 | | | 3 | 3 | | | 4 | 3 |
| Dead nettle | | 3 | 2 | 2 | | 3.5 | 2 | 2 | | | 2 | 2 | | | 2 | 2 | | | 2 | 2 |
| Bent grass | 2 | 2 | 1 | 1 | 2 | 2 | 1 | 1 | 4 | 3 | 1 | 1 | 3 | 3 | 2 | 1.5 | 5 | 3 | 3 | 1.5 |

1 = completely effective; plant killed
5 = no effect; plant appears as if untreated

| | |
|---|---|
| White mustard | *Sinapis alba* |
| Tomato | *Solanum lycopersicum* |
| Oats | *Avena sativa* |
| Barnyard grass | *Echinochloa crusgalli* |
| Wild oats | *Avena fatua* |
| Field foxtail | *Alopecurus myosoroides* |
| Chickweed | *Stellaria media* |
| Bedstraw | *Gallium aparine* |
| Cornflower | *Centaurea cyanus* |
| Camomile | *Anthemis spec.* |
| Dead nettle | *Lamium purpureum* |
| Hemp nettle | *Galeopsis tetrahit* |
| Wild beet | *Amaranthus retroflexus* |
| White goosefoot | *Chenopodium album* |
| Vetch | *Vicia angustifolia* |
| Sugar beet | *Beta vulgaris* |
| Turnip | *Brassica rapa* |
| Knot grass | *Polygonum spec.* |
| Maize | *Zea mays* |
| Corn poppy | *Papaver rhoeas* |
| Pansy | *Viola arvensis* |
| Green foxtail | *Setaria viridis* |
| Hairy crabgrass | *Digitaria sanguinalis* |
| Crabgrass | *Digitaria ischaemum* |
| Spring barley | *Hordeum vulgare* |
| Spring wheat | *Triticum aestivum* |
| Bent grass | *Apera spica-venti* |
| Winter barley | *Hordeum sativum* |
| Winter wheat | *Triticum aestivum* |
| Rye | *Secale cereale* |
| Quack grass | *Agropyron repens* |

What is claimed as new and desired to be secured by Letters Patent of the United States is:

1. α-Substituted N-(trimethylcycloalkenyl)-N-alkylacetamides of the formula

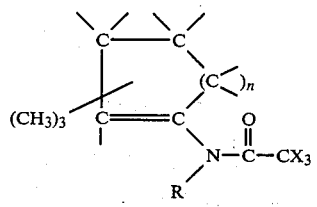

wherein R represents a linear or branched alkyl or alkoxyalkyl radical having 1-6 carbon atoms or an allyl radical optionally sutstituted with $C_1$-$C_4$ alkylene groups, and X is a substituent from the group consisting of hydrogen, methyl, chlorine, and bromine in any combination, n is an integer equal to 1 or 2, the free valences represent hydrogen and two of the methyl groups on the ring are attached to the same ring carbon atom.

2. The acetamide of claim 1 having the formula

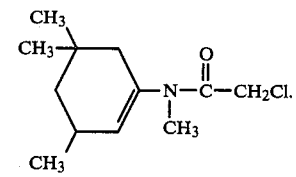

3. The acetamide of claim 1 having the formula

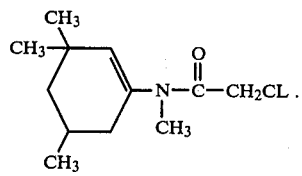

4. The acetamide of claim 1 having the formula

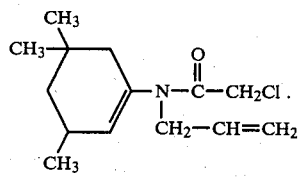

5. The acetamide of claim 1 having the formula

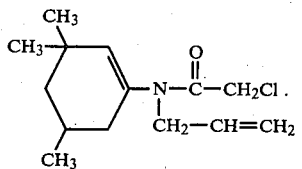

6. A mixture comprising two acetamides according to claim 1 having the formulas

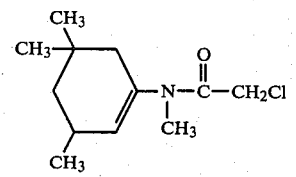

and

-continued

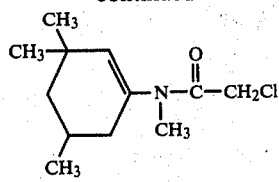

wherein each of said acetamides is present in a proportion of at least 1% by weight.

7. A mixture comprising two acetamides according to claim 1 having the formulas

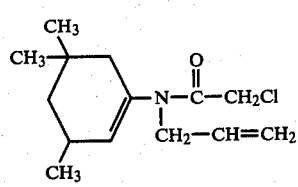

and

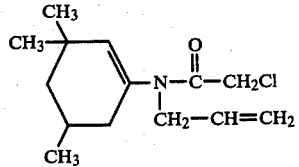

wherein each of said acetamides is present in a proportion of at least 1% by weight.

8. An acetamide of claim 1 having the formula

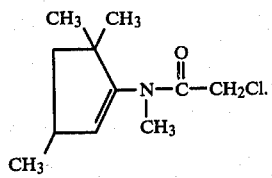

9. An acetamide of claim 1 having the formula

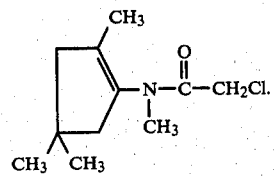

10. An acetamide of claim 1 having the formula

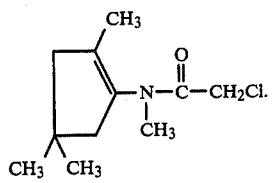

11. An acetamide of claim 1 having the formula

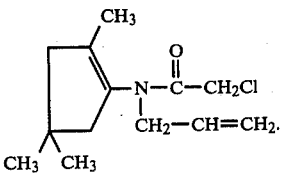

12. An acetamide of claim 1 having the formula

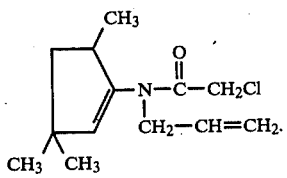

13. A mixture containing at least two of the acetamides of claims 7, 8, 9, 10 or 11, wherein said acetamides are present in the mixtures in proportions of at least 1% by weight.

14. An herbicidal composition comprising a compound of claim 1 and an adjuvant selected from the group consisting of carriers, fillers, diluents, wetting agents, dispersants and emulsifiers.

15. A process for killing weeds in the presence of crops comprising applying to the crop an herbicidal compound of claim 1.

16. The process of claim 15 wherein said herbicidal compound is applied before the emergence of the crop plants.

17. The process of claim 15 wherein said herbicidal compound is applied after the emergence of the crop plants.

18. The process of claim 15 wherein said herbicidal compound is applied as a mixture of said herbicidal compound with an adjuvant selected from the group consisting of carriers, fillers, diluents, wetting agents, dispersants, and emulsifiers.

* * * * *